(12) United States Patent
Kraft

(10) Patent No.: US 6,370,420 B1
(45) Date of Patent: Apr. 9, 2002

(54) SYSTEM AND METHOD FOR OBJECTIVELY VERIFYING AN INTERNAL DISC DISRUPTION

(76) Inventor: Mark Kraft, 3920 Youngson Dr., Las Vegas, NV (US) 89121

( * ) Notice: Subject to any disclaimer, the term of this patent is extended or adjusted under 35 U.S.C. 154(b) by 0 days.

(21) Appl. No.: 09/193,800

(22) Filed: Nov. 17, 1998

(51) Int. Cl.[7] .................................................. A61B 5/00
(52) U.S. Cl. .................... 600/431; 604/51; 600/561; 600/301; 600/587; 600/407; 348/77
(58) Field of Search ......................... 600/431, 407, 600/561, 587, 300, 301; 128/902, 903, 920, 904; 604/51, 49, 93, 95; 348/77

(56) References Cited

U.S. PATENT DOCUMENTS

| | | | | |
|---|---|---|---|---|
| 3,964,480 A | * | 6/1976 | Froning | 128/214 |
| 5,203,346 A | * | 4/1993 | Fuhr et al. | 128/781 |
| 5,458,119 A | * | 10/1995 | Vanharanta | 128/744 |
| 5,544,649 A | * | 8/1996 | David et al. | 128/630 |
| 5,647,361 A | * | 7/1997 | Damadian | 128/683.2 |
| 5,694,946 A | * | 12/1997 | Tenerz | 128/748 |
| 5,980,504 A | * | 11/1999 | Sharkey et al. | 604/510 |
| 6,007,459 A | * | 12/1999 | Burgess | 482/1 |
| 6,283,961 B1 | * | 9/2001 | Underwood et al. | 606/41 |

* cited by examiner

*Primary Examiner*—Marvin M. Lateef
*Assistant Examiner*—Eleni Mantis Mercader
(74) *Attorney, Agent, or Firm*—Philip J. Anderson; Anderson & Morishita

(57) ABSTRACT

A device is provided for diagnosing internal disc disruption in an intervertebral disc in a patient's spine. A needle is used for injecting a contrast media with increasing pressure into the nucleus pulposis of one of the patient's intervertebral discs suspected to be disrupted are provided. As the pressure of the contrast media in the patient's intervertebral disc is increased, a measurement of the pressure, photographic images of the patient's facial expressions, x-ray images of the patient's intervertebral disc are displayed simultaneously and in real time on a display. In addition, the patient's vocalizations are captured and broadcast by the display. A recorder for recording the images on the display and the vocalizations may also be provided.

5 Claims, 3 Drawing Sheets

SYSTEM AND METHOD FOR OBJECTIVELY VERIFYING AN INTERNAL DISC DISRUPTION

FIELD OF THE INVENTION

The present invention relates to devices for diagnosing internal disc disruption in intervertebral discs. More specifically, the present invention uses pressurized contrast media to distend a patient's intervertebral disc and displays objective indicia of the existence of back pain and the existence and severity of Internal Disc Disruption (IDD).

BACKGROUND OF THE INVENTION

Back pain can have a variety of causes, one of which is an internally injured intervertebral disc. Intervertebral discs are cushions of fibrocartilage between adjacent vertebrae of the spine. Each intervertebral disc is composed of a nucleus pulposis surrounded by an anulus fibrosus. When the nucleus pulposis degrades or is traumatically injured, fissures may form in the anulus fibrosus. An intervertebral disc degraded or injured in this fashion is said to have internal disruption. Fissures in the anulus fibrosus can cause back pain because: (1) the innervated outer section of the anulus fibrosus is injured and becomes painful when exposed to pressure; (2) the injured anulus fibrosus must bear the load previously supported by the healthy anulus fibrosus; and (3) the nerve endings in the fissured anulus fibrosus are exposed to the caustic and inflammatory intranuclear contents of the disc.

There is no reliable method or device in the prior art which can accurately diagnose a symptomatic and disrupted intervertebral disc. This is partly attributed to the fact that an internally disrupted intervertebral disc, unlike a herniated intervertebral disc, may not show any outward signs of abnormality. Thus, the most common diagnostic method, called disc stimulation or a discogram, is to inject saline or a contrast medium into the nucleus pulposis of an intervertebral disc suspected to be internally disrupted. The pressure of the injected fluid on the anulus fibrosus distends the intervertebral disc. If the intervertebral disc is not internally disrupted, the anulus fibrosus will withstand the pressure of the fluid and the patient should feel no pain. If the intervertebral disc is disrupted, the pressure of the injected fluid on the innervated section of the anulus fibrosus will reproduce the patient's back pain. Thus, if the patient indicates that the pressurized injection causes the patient back pain, then the intervertebral disc which was injected is symptomatic.

However, this procedure has its drawbacks. First, there is no objective way to confirm the existence of pain. Thus, the procedure is entirely dependent on the patient's ability to perceive and report the pain accurately.

Moreover, the prior art procedure only measures a single factor, the patient's pain. In other words, disc stimulation has not previously provided objective measurements of the existence or severity of fissuring. Thus, disc stimulation used alone may misdiagnose an internally disrupted intervertebral disc because some condition other than an internally disrupted intervertebral disc may cause pain in the patient. While a CT x-ray scan may be performed after the disc stimulation to confirm fissuring in a intervertebral disc, disc stimulation must first be used to determine which intervertebral discs are symptomatic.

Thus, it is clear that there is a need in the art for an apparatus which provides objective measures of the presence of pain and the existence and degree of fissuring to diagnose, or confirm a diagnosis of, an internally disrupted intervertebral disc.

SUMMARY OF THE INVENTION

A device for diagnosing or confirming a diagnosis of a symptomatic internal disruption in an intervertebral disc in a patient's spine is disclosed herein. A needle in fluid communication with a fluid source containing fluid contrast media is inserted into the patient's spine so that the end of the needle rests in the nucleus pulposis of an intervertebral disc suspected to be disrupted. Contrast media is visible to an x-ray camera or a fluoroscope. The pressure of the contrast media delivered to the patient's intervertebral disc is gradually increased.

Means are provided to measure the volume and pressure of the contrast media, take realtime videographic images of the patient's facial expressions, obtain x-ray images of the patient's intervertebral disc, and capture the patient's vocalizations as the contrast media is injected into the patient's intervertebral disc. In a preferred embodiment, a pressure sensor measures the pressure of the contrast media. Simultaneously, a video camera takes photographic images of the patient's facial expressions, an x-ray camera takes x-ray images of the patient's intervertebral disc, and a microphone captures the patient's vocalizations. The pressure measurements, photographic images, x-ray images, and vocalizations are transmitted to a display. The display simultaneously and in real time displays on a single screen the photographic images, x-ray images, and pressure measurements. A speaker in the display also broadcasts the vocalizations. The present invention may include a video cassette recorder to record the displayed images and the patient's vocalizations, a computer to digitally capture the displayed images and vocalizations, and a printer to prepare output copies of the displayed images.

A medical professional monitors the display. If the intervertebral disc is not internally disrupted, the patient should show no visible or audible indicia of pain such as uncomfortable or pained facial expressions or pained vocalizations. By contrast, if the intervertebral disc is symptomatically disrupted, the pressurized fluid will fill the fissures in the anulus fibrosus and press on the innervated outer section of the anulus fibrosis thereby reproducing the patient's back pain. Thus, the patient's pained facial expressions will be visible in the photographic images displayed and the patient's pained vocalizations will be audible over the audio broadcast.

Also, if there is no fissuring, the intervertebral disc should be able to withstand a fluid pressure of at least 75 pounds per square inch, the pressure the intervertebral disc must bear during normal sitting or stooping. Conversely, if the intervertebral disc is internally disrupted, the intervertebral disc will be able to withstand much less pressure as the fissures are forced apart and, in the most severe cases, allow the contrast media to escape the intervertebral disc. A pain response at a pressure of less than 50–75 pounds per square inch would tend to indicate that the intervertebral disc is symptomatically disrupted.

Also, if there is no fissuring of the anulus fibrosus, the anulus fibrosus should contain the injected contrast media in the nucleus pulposis and the x-ray photographs should show no spreading of the contrast media beyond the horseshoe-shaped nucleus pulposis. If, however, the intervertebral disc is internally disrupted, the x-ray photographs will show the contrast media spreading through the fissures into the anulus fibrosus.

These measurements and images in combination are used by the medical professional to determine whether the intervertebral disc is internally disrupted. For example, a pain response at a pressure of less than 50–75 pounds per square inch in combination with x-ray images showing internal disc disruption would indicate that the intervertebral disc is symptomatically injured.

An object of the present invention is to provide a device which accurately and reliably diagnoses a symptomatic and disrupted intervertebral disc. It is a further object of the present invention to provide a medical professional with objective information in real time of the existence of pain in a patient and the existence and severity of fissuring in a patient's intervertebral disc as the intervertebral disc is injected with contrast media. Also, it is an object of the present invention to provide objective data to confirm and support a medical professional's conclusion and diagnosis. An additional object of the invention is to provide a display which simultaneously displays photographic images, x-ray images, and pressure readings on a single screen and provides an audio broadcast of the patient's vocalizations so that a medical professional will be able to access all the relevant information without viewing numerous displays or switching between input channels on a display. A further object of the invention is to provide a device which can preserve the displays and audio broadcast for later use as evidence of the condition of the intervertebral disc. This allows other medical professionals to review the test results as if they were present at the time of the test. Another object of the invention is to standardize the parameters for diagnosis of internal disc disruption by decreasing interoperator variability in performing or interpreting the test.

DESCRIPTION

Figure 1:
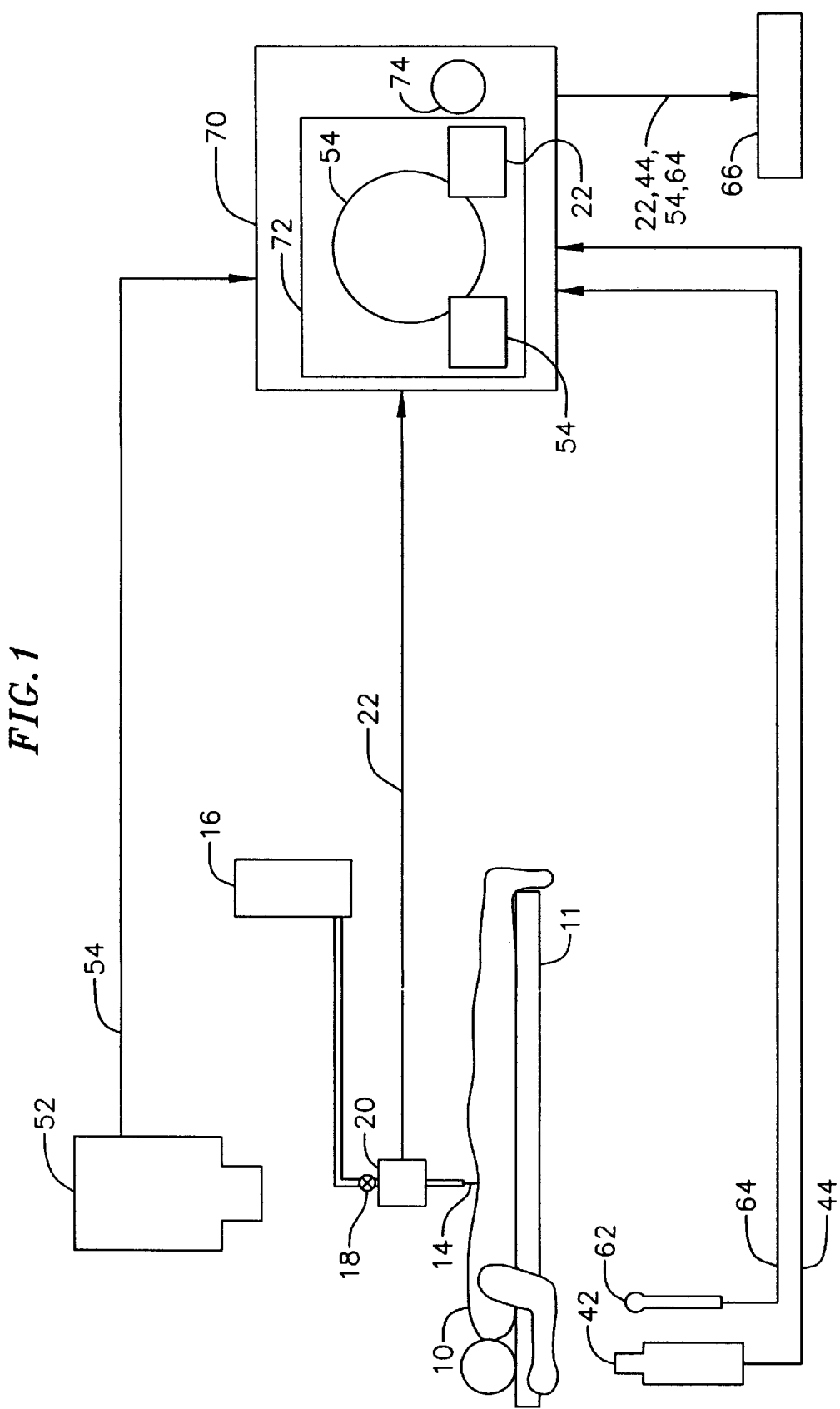
FIG. 1 is a schematic of the device of the present invention.

Reference is now made to the figures wherein like parts are referred to by like numerals throughout. Referring to FIG. 1, a patient 10 lies in a prone position on an examining table 11 with his back exposed. A hollow needle 14 is in fluid communication with a fluid source 16 containing a contrast media. The contrast media is a fluid which is opaque to x-rays and, thus, provides an image of the interior structure of the patient's intervertebral disc 24 in x-ray photographs. A valve 18 disposed between the needle 14 and the fluid source 16 controls the volume and pressure of contrast media delivered to the needle 14.

Figure 2:
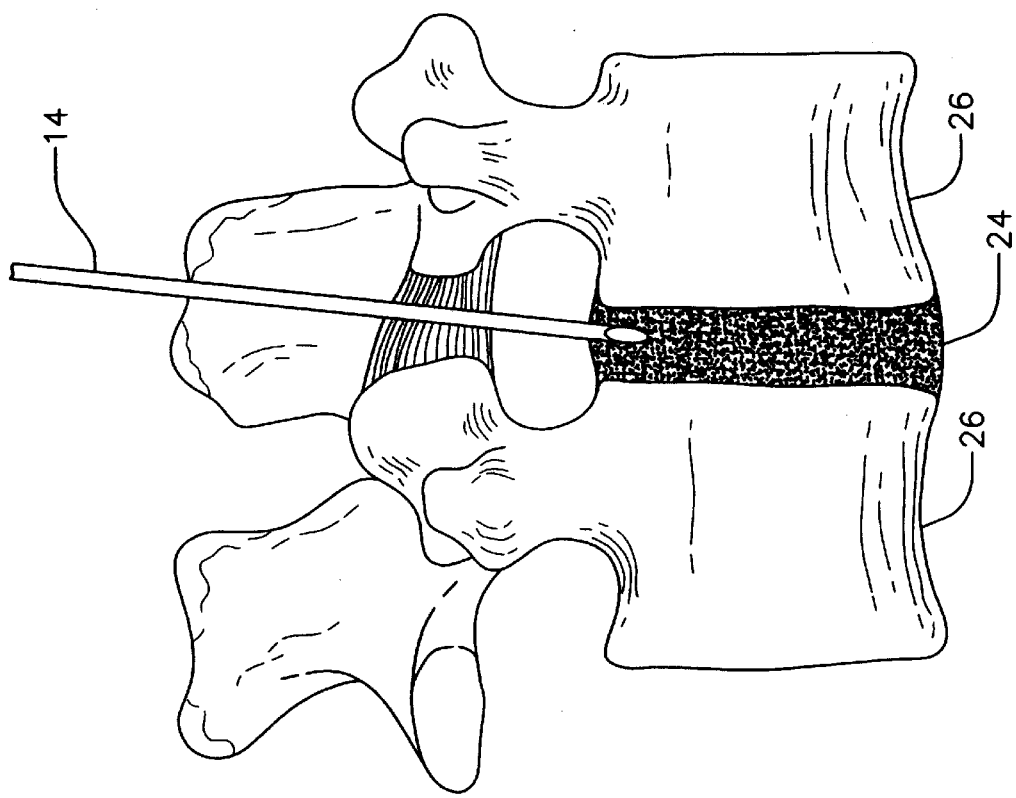
FIG. 2 is a left side view of a patient's spine as a needle is inserted into an intervertebral disc.
Figure 3:
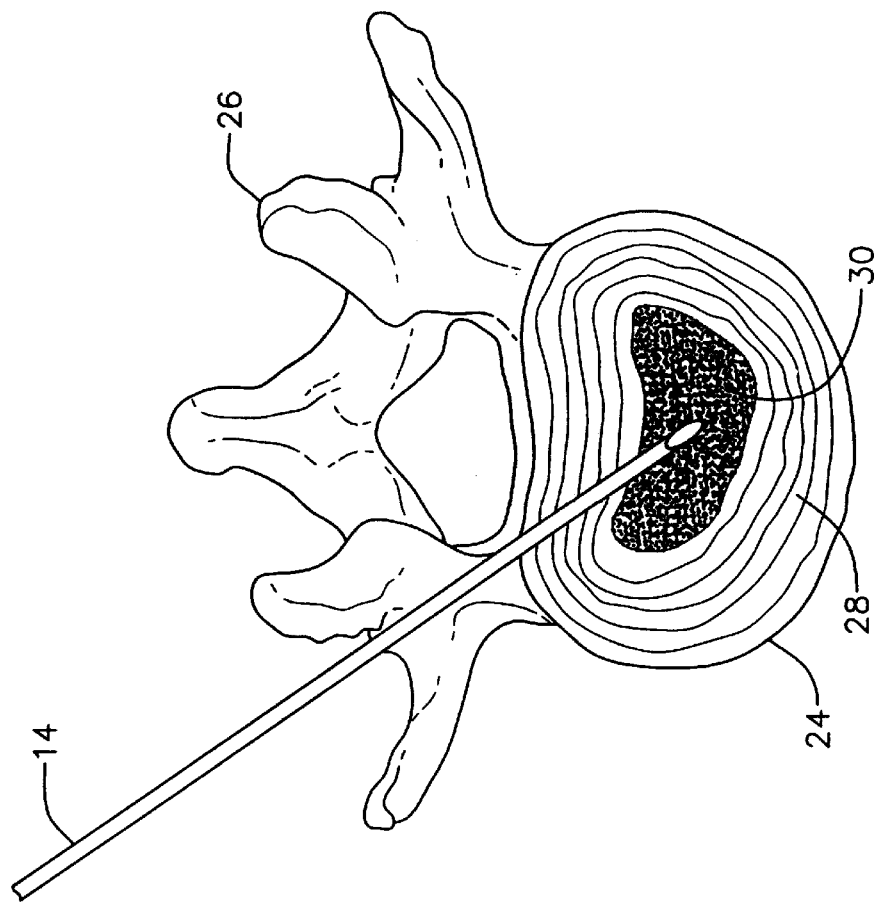
FIG. 3 is a top view of a patient's intervertebral disc along line A—A of FIG. 2.

As shown in FIG. 2, the intervertebral disc 24 is a cushion between two adjacent vertebrae 26 in the patient's 10 spine. The needle 14 is inserted into the intervertebral disc 24 suspected of being internally disrupted. Referring to FIG. 3, the intervertebral disc 24 is composed of a nucleus pulposis 30 surrounded by the anulus fibrosus 28. The end of the needle 14 is inserted through the anulus fibrosus 28 until it rests in the nucleus pulposis 30 of the intervertebral disc 24. Referring again to FIG. 1, the valve 18 is slowly opened to gradually increase the pressure and volume of fluid delivered to the nucleus pulposis 30 through the needle 14.

Means for measuring the pressure of the fluid delivered to the needle 14 and transmitting the pressure measurements 22 to the display 70 are in fluid communication with the needle 14. The means could be a pressure sensor 20 which measures the pressure of the fluid, converts the pressure measurement 22 into an electrical signal, and transmits the pressure measurement 22 to the display 70. Alternatively, the means could be a pressure sensor 20 and a video camera which takes a photographic image of the pressure sensor's 20 reading and transmits the photographic image of the pressure reading to the display 70.

Means for taking photographic images 44 of the patient's facial expressions and transmitting those photographic images 44 to the display 70 are provided. In a preferred embodiment, the means is a conventional video camera 42 which takes photographic images 44 of the patient's face, converts the images into an electrical signal, and transmits the photographic images 44 to the display 70.

The present invention also includes means for taking real time x-ray images 54 of the intervertebral disc 24 being injected with the contrast media and transmitting the x-ray images 54 to the display 70. The means is preferably an x-ray camera 52 conventional in the art which exposes the intervertebral disc 24 to x-ray radiation, forms an x-ray image 54 from the x-rays not absorbed by the tissue, and transmits the x-ray image 54 to the display 70.

The present invention includes means for capturing the patient's vocalizations 64 and transmitting the vocalizations 64 to a speaker 74. Preferably the speaker 74 is in the display 70. In a preferred embodiment, the means is a conventional microphone 62 having a diaphragm which vibrates in response to the patient's vocalizations 64 and thereby converts the vocalizations 64 into electrical signals. The electrical signals are then transmitted to the speaker 74 where the vocalizations 64 are broadcast.

The display 70 includes a screen 72 and speaker 74. The display 70 receives and broadcasts the transmitted vocalizations 64 through a conventional speaker 74. The display 70 simultaneously receives and displays the pressure measurements 22, photographic images 44, and x-ray images 54 on a conventional screen 72. The screen 72 could be a cathode ray tube screen, a liquid crystal display, or the like. The images are arranged on a single screen 72 so that a medical professional may view all of the images without scrolling through different displays or changing channels. In a preferred embodiment, the x-ray image 54 is centered on the screen 72 with the pressure measurements 22 and photographic images 44 to either side. The screen 72 may additionally display information such as the patient's name, the date, the time, the time elapsed, the name of the medical professional, the location of the intervertebral disc 24 being tested, and the like.

In a preferred embodiment, the present invention includes a means for recording the vocalizations 64, photographic images 44, pressure measurements 22, and x-ray images 54 received at the display 70. The means is preferably a video cassette recorder 66 receiving output from the display 70 so that the images and sound recorded are identical to those displayed and broadcast by the display 70. Alternatively, a video cassette recorder 66 could receive the vocalizations 64, photographic images 44, pressure measurements 22, and x-ray images 54 directly from the means collecting the sounds and images.

Figure 5:
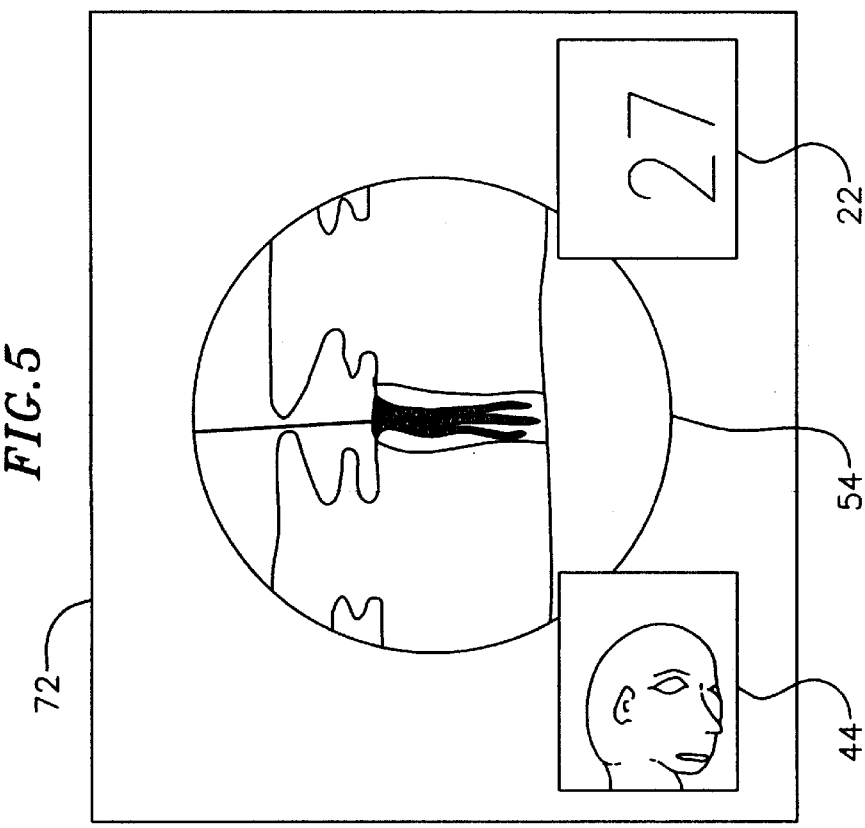
FIG. 5 is an enlarged view of the display of the present invention as contrast media is injected into an internally disrupted intervertebral disc.
Figure 4:
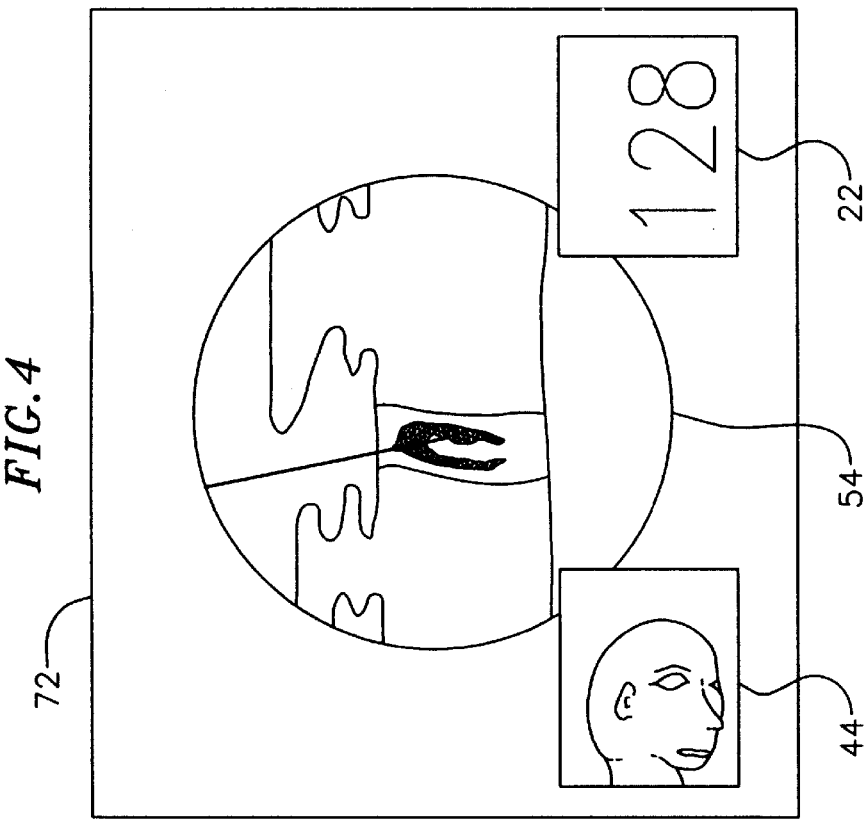
FIG. 4 is an enlarged view of the display of the present invention as contrast media is injected into a healthy intervertebral disc.

A physician or trained medical professional controls the pressure of the contrast media delivered to the patient's intervertebral disc 24. The medical professional monitors the images and sounds at the display 70 as the pressure of the contrast media delivered to the patient's intervertebral disc 24 is increased. In a healthy intervertebral disc 24, the pressure of the contrast medium will not cause pain because the anulus fibrosus 28 will easily withstand the pressure of the fluid contrast medium. However, if the anulus fibrosus 28 is fissured, the contrast medium will fill the fissures and press against the innervated outer section of the anulus fibrosus 28 causing back pain in the patient. As the pain is felt by the patient, the patient will likely react with a contorted or pained facial expression. Thus, a medical professional will look at the photographic images 44 on the screen 72 of the display 70 for a pained facial expression as indicating an internally disrupted intervertebral disc 24. For example, the photographic image 44 shown on the display of FIG. 5 shows a patient with a pained facial expression. By contrast, the photographic image 44 shown on the display of FIG. 4 shows a patient without a pained facial expression. Also, the pain is likely to elicit some audible response from the patient. Thus, a medical professional will listen to the vocalizations 64 broadcast by the speaker 74 of the display 70 to determine whether the patient is experiencing pain.

Further, a healthy intervertebral disc 24 must normally withstand 75 pounds per square inch (psi) during sitting or stooping. Thus, as the pressure of the contrast medium is increased, the pressure measurements 22 on the screen 72 of the display 70 should indicate at least 75 psi for a healthy intervertebral disc 24. For example, the pressure measurement 22 shown in FIG. 4 shows that the contrast medium in the intervertebral disc 24 has a pressure of 128 psi. By contrast, an internally disrupted intervertebral disc 24, shown in FIG. 5, will be able to withstand far less than 75 psi because the pressurized contrast medium will force the fissures to spread apart and, possibly, allow the contrast medium to escape from the intervertebral disc 24. Thus, the medical professional will look for a maximum pressure measurement on the screen 72 of the display 70 of less than 75 psi as an indicator of an internally disrupted intervertebral disc 24. For example, the pressure measurement 22 shown in FIG. 5 indicates that the contrast medium in the intervertebral disc 24 has a pressure of 47 psi. Also, in an internally disrupted intervertebral disc 24, the medical professional would expect to elicit a pain response at a pressure of less than 75 psi. Thus, the medical professional would examine the pressure measurement displayed at the point where the photographic images 44 and vocalizations 64 indicate the patient is experiencing pain to determine whether the pain is caused by an internally disrupted intervertebral disc 24.

Finally, if the intervertebral disc 24 is healthy, the anulus fibrosus 28 of the intervertebral disc 24 will contain the contrast medium in the nucleus pulposis 30. Thus, the x-ray images 54 will show that the contrast medium is confined to the horseshoe-shaped nucleus pulposis 30 of a healthy intervertebral disc 24, as shown in FIG. 4. However, if the intervertebral disc 24 is internally disrupted, contrast medium will fill the fissures and possibly escape from the intervertebral disc 24. Thus, as shown in FIG. 5, a medical professional will look for x-ray images 54 on the screen 72 of the display 70 which show the contrast medium spreading through the intervertebral disc 24 and possibly leaking from the intervertebral disc 24 in addition to the pressure readings and the indicia of pain, as indicating an internally disrupted intervertebral disc 24.

An advantage of the present invention is that the device provides objective indicia, such as pressure measurements 22 and real time x-ray images 54, to indicate the existence and severity of fissuring. Also, objective indicia of the existence of pain, such as photographic images 44 and the patient's vocalizations 64, assist the medical professional in determining whether the patient's back pain has been reproduced. By combining all these indicia on a single display 70, the present invention has the advantage of giving the medical professional the necessary information to diagnose the intervertebral disc 24 disruption without having to scroll through screens, view several different screens, or change input channels while performing the diagnosis. Another advantage of the present invention is that the images and sounds are presented simultaneously and in real time so that the medical professional may properly account for the interdependency of each of the various measurements, images, and sounds to determine if, as a whole, the measurements, images, and sounds indicate an internally disrupted intervertebral disc 24. Yet another advantage of the present invention is that the present invention may be used to accurately record the condition of a patient's intervertebral disc 24 and the process of diagnosis by recording the images displayed and the vocalizations 64 broadcast on the display 70. Also, the data obtained may be used to objectively confirm and support a medical professional's conclusions and diagnosis by insurance companies and in litigation.

While the invention has been particularly shown and described with reference to a preferred embodiment thereof, it should be understood by those skilled in the art that changes in form and detail may be made therein without departing from the spirit and scope of the claims.

I claim:

1. A device for diagnosing internal disc disruption in an intervertebral disc in a patient's spine comprising:
   a needle for injecting a contrast media with increasing pressure into the nucleus pulposis of one of the patient's intervertebral discs suspected to be disrupted;
   a display having a screen;
   a speaker;
   a pressure sensor for measuring the pressure of the contrast media during injection into the suspected intervertebral disc and transmitting said pressure measurements to said display;
   a camera for capturing images of the patient's facial expression during said injection and transmitting said images to said display;
   means for taking x-ray images of the suspected intervertebral disc and transmitting said x-ray images to said display during injection of said media under increasing pressure; and
   a microphone for capturing the patient's vocalizations and transmitting said vocalizations to said speaker, said device simultaneously displaying at the display said pressure, x-ray images, facial expressions during injection of said media; and
   a recorder to record said display and vocalizations to define an objective record concerning said suspected disc.

2. The device of claim 1 wherein the recorder is a video cassette recorder.

3. The device of claim 1 wherein said speaker is disposed in said display.

4. A device for diagnosing internal disc disruption in an intervertebral disc in a patient's spine including a fluid contrast media visible in x-ray images, said device comprising:

a source of contrast media under pressure;

a hollow needle in fluid communication with said source, said needle inserted into the nucleus pulposis of the patient's intervertebral disc suspected to be disrupted;

a valve disposed between said source and said needle to control the pressure of contrast media delivered through said needle to the patient's intervertebral disc;

a display having a screen;

a speaker;

a pressure sensor in fluid communication with said needle for measuring the pressure of the contrast media delivered to the patient's intervertebral disc and transmitting said pressure measurements to said display for display of the pressure as said contrast media is delivered to the disc;

a video camera for taking photographic images of the patient's facial expression and transmitting said photographic images to said display to display with said pressure;

an x-ray camera for taking x-ray images of the patient's intervertebral disc suspected of being disrupted and transmitting said x-ray images to said display to display with said pressure, said x-ray images and injected contrast media show disc disruption and the pressure at such disruption as well as the patient's expression at disruption; and a microphone for capturing the patient's vocalizations and transmitting said vocalizations to said speaker, and a video cassette recorder for recording the vocalizations and the displays of said pressure measurements, photographic images, and x-ray images.

5. A device for diagnosing internal disc disruption in an intervertebral disc in a patient's spine including a fluid contrast media visible in x-ray images, said device comprising:

a source of liquid contrast media under pressure;

a needle in fluid communication with said source, said needle inserted into the nucleus pulposis of the patient's intervertebral disc suspected to be disrupted;

a valve to increase the pressure of contrast media delivered through said needle to the patient's intervertebral disc and to relieve the pressure;

a display having a screen;

a pressure sensor in fluid communication with said needle for measuring the pressure of the contrast media delivered to the patient's intervertebral disc and transmitting said pressure measurements to said display for display of the pressure as said contrast media is delivered to the disc;

a video camera for taking photographic images of the patient's facial expression and transmitting said photographic images to said display to display with said pressure;

an x-ray camera for taking x-ray images of the patient's intervertebral disc suspected of being disrupted and transmitting said x-ray images to said display to display with said pressure as said pressure of the contrast media is increased, said x-ray images and injected contrast media showing disc disruption and the pressure at such disruption as well as the patient's expression at disruption; and a microphone for capturing the patient's vocalizations and transmitting said vocalizations to said speaker; and a video cassette recorder for recording the vocalizations and the displays of said pressure measurements, photographic images, and x-ray images.

* * * * *